United States Patent [19]

Bokros

[11] Patent Number: 4,863,467
[45] Date of Patent: Sep. 5, 1989

[54] HEART VALVE PROSTHESIS WITH LEAFLETS VARYING IN THICKNESS AND HAVING SPHERICAL EARS

[75] Inventor: Jack C. Bokros, Austin, Tex.
[73] Assignee: Carbomedics Inc., Austin, Tex.
[21] Appl. No.: 284,104
[22] Filed: Dec. 14, 1988
[51] Int. Cl.[4] ............................................. A61F 2/24
[52] U.S. Cl. .................................... 623/2; 137/512.1; 137/527
[58] Field of Search ................. 623/2; 137/512.1, 527, 137/527.8

[56] References Cited

U.S. PATENT DOCUMENTS

| | | | |
|---|---|---|---|
| 4,308,624 | 1/1982 | Klawitter | 623/2 |
| 4,357,715 | 11/1982 | Klawitter | 623/2 |
| 4,443,894 | 4/1984 | Klawitter | 623/2 |
| 4,451,937 | 6/1984 | Klawitter | 623/2 |
| 4,689,046 | 8/1987 | Bokros | 623/2 |

FOREIGN PATENT DOCUMENTS 0211576 2/1987 European Pat. Off. ................. 623/2

Primary Examiner—Ronald L. Frinks
Attorney, Agent, or Firm—Russell J. Egan; John R. Merkling

[57] ABSTRACT

A heart valve prosthesis having an annular valve body, a pair of leaflet occluders mounted therein for pivoting and translational movement between closed and open positions. The leaflet occluders have mating diametrical edges and arcuate edges which engage the valve body when the leaflets are closed. Generally part spherical mounting ears extend outwardly from the leaflet edge, adjacent the diametrical edge thereof. The ears are received in crescent-shaped recesses formed in the annular body. The recesses have opposed upstream and downstream surfaces for guiding the mounting ears during opening and closing of the leaflet.

10 Claims, 2 Drawing Sheets

U.S. Patent  Sep. 5, 1989  Sheet 1 of 2  4,863,467
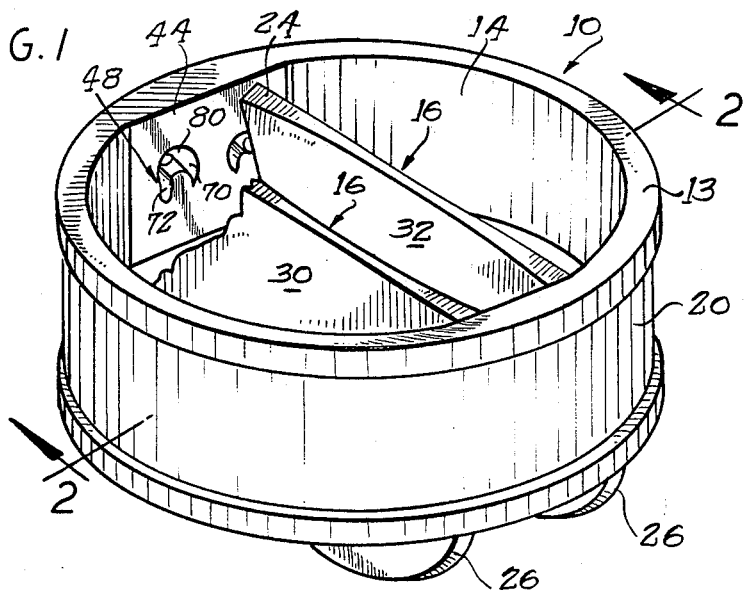
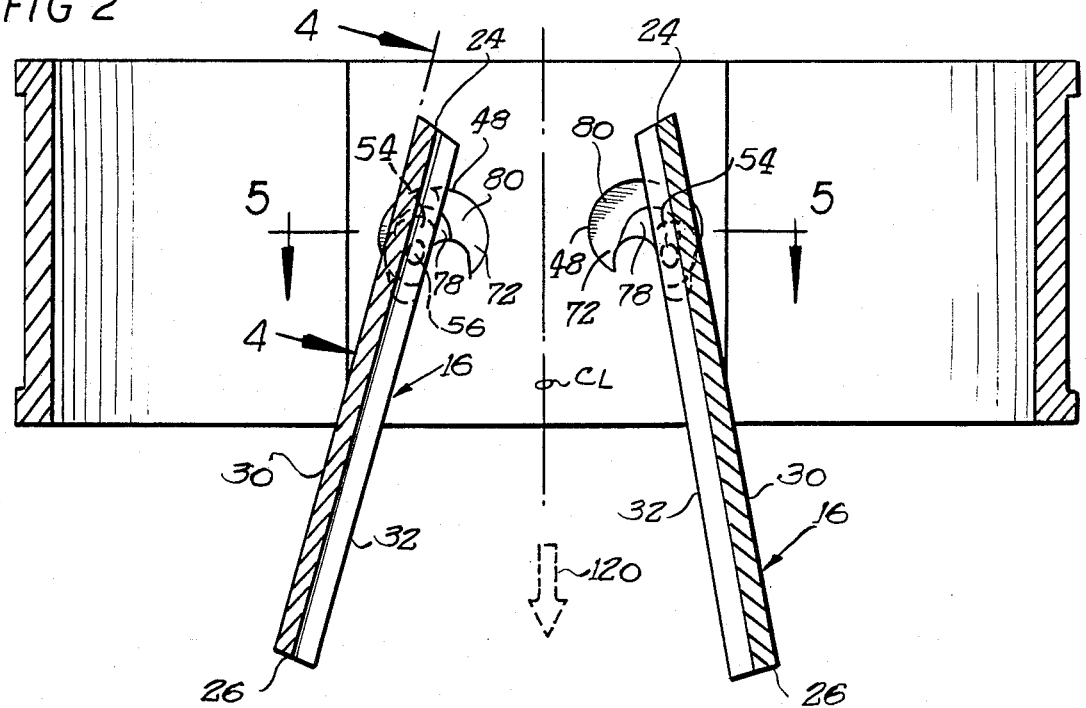
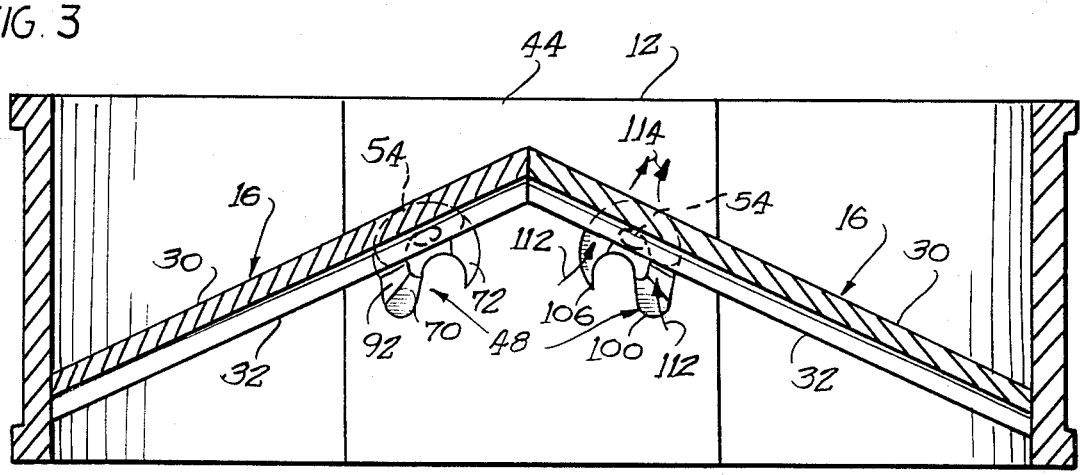

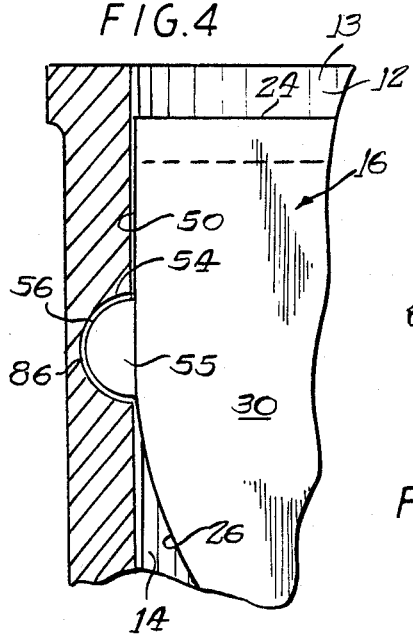
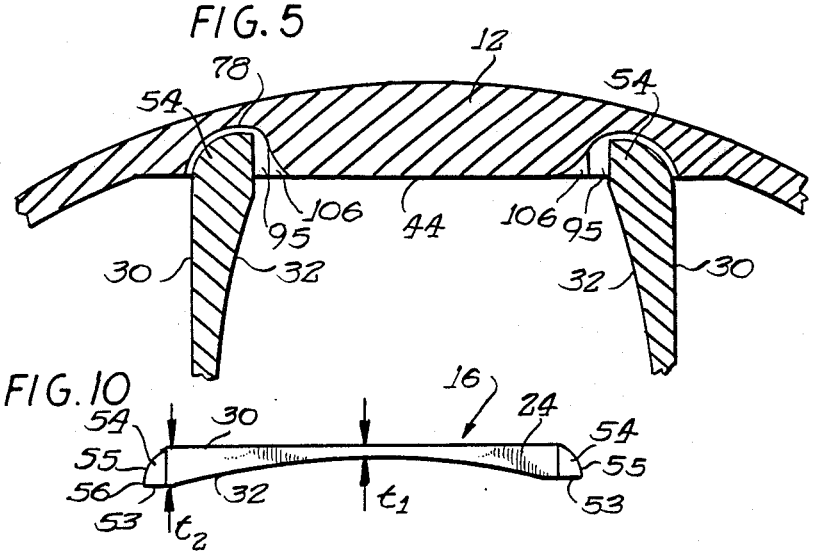
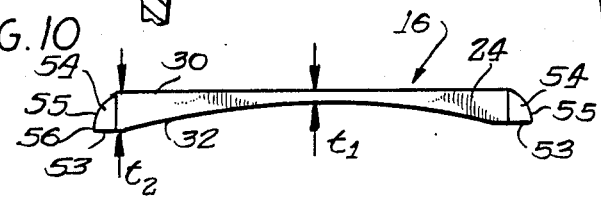
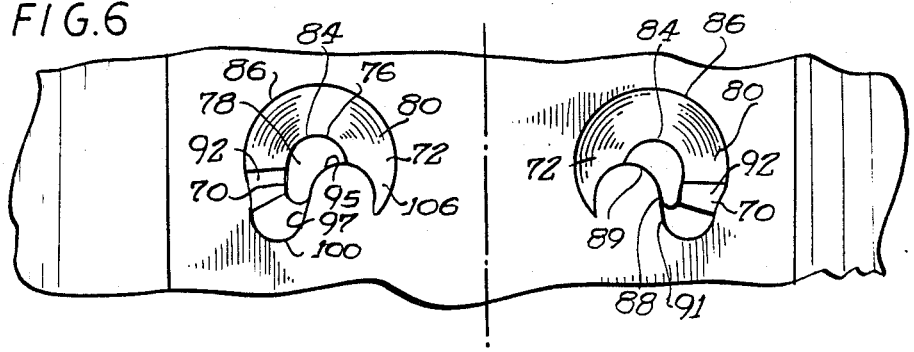
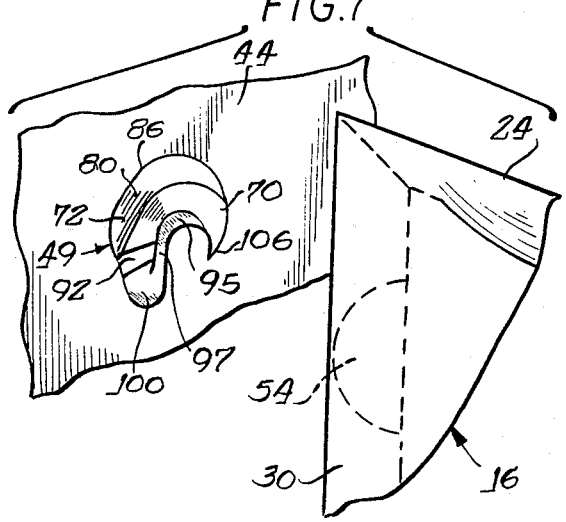
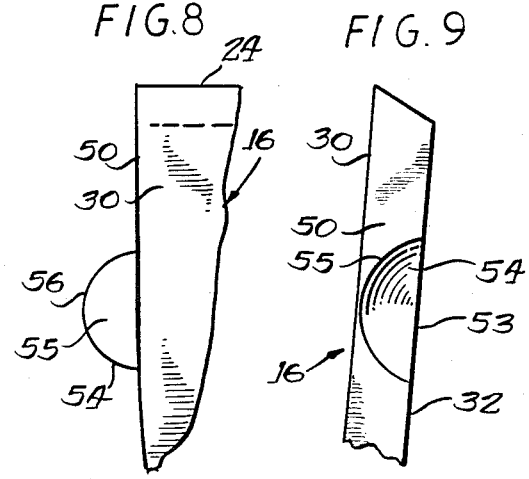

HEART VALVE PROSTHESIS WITH LEAFLETS VARYING IN THICKNESS AND HAVING SPHERICAL EARS

BACKGROUND OF THE INVENTION

1. Field of the Invention

The present invention pertains to heart valve prostheses and in particular, to bileaflet heart valve prostheses using pivotable valve members.

2. Description of Related Art

Various types of heart valve prostheses have been proposed, and many give generally satisfactory operation and have lifetimes longer than the life expectancy of the patient who is to wear the prosthesis. One popular design for a heart valve prosthesis included an annular valve body in which a pair of opposed leaflet occluders are pivotally mounted. The occluders are movable between a closed, mated position so as to block blood flow in an upstream direction, and an open position allowing blood flow in a downstream direction.

Several improvements to heart valve prostheses are still desired. For example, in order to reduce assembly costs and in order to minimize any difficulties arising from variations in assembly techniques, it is desirable to provide leaflet occluders which may be fitted to the valve body by temporarily distorting the leaflet occluders so as to permit their snap-in engagement within recesses formed in the valve body. Once installed, it is particularly desirable that the leaflet occluders be free to move within the valve body with minimal friction.

Also, it is particularly desirable that a heart valve prosthesis be provided which suffers no appreciable change in operating efficiency, at least over the life of a patient wearing the prosthesis.

In another area of potential improvement, it is desirable to impart a more rapid closing time to the leaflet occluders so as to reduce regurgitation. However, such quickening of the closing time should not be accompanied by an increase of frictional wear of the leaflet mounting parts, even if such increased wear results only in relatively minor aberrations of the occluder movement.

Further, although it is desirable to have closing time as rapid as possible, this should not be accompanied by an increase in noise during operation of the prosthesis, for example, as the leaflet occluders engage the valve body as they seat there against to block any regurgitation that might otherwise occur.

In a bi-leaflet type of heart valve prosthesis, the leaflet occluders typically engage each other along diametral edges, and engage portions of the valve body at points remote from the diametral edges. Such engagement should not give rise to clicking or other such noises, even though the closing time thereof is significantly shortened.

Also, any rebounding of the leaflets should be controlled so as to prevent any unnecessary wear, and also to conserve hemodynamic energy which operates the prosthesis. In particular, it is important that any decreases in valve closing time do not contribute to rebounding of the leaflets, as might otherwise be expected.

In the past, leaflet occluders have occasionally been slightly undersized so as to allow a purging blood flow therearound, even when the leaflets are closed. Such flows wash over localized, edge surfaces of the leaflets and the valve body to prevent any clotting that might occur at those locations. It is important, however, that hemodynamic energy of a patient be conserved as much as possible and accordingly it is important that the amount of undersizing of the leaflet occluders be accurately controlled. Such sizing, of course, depends upon manufacturing tolerances in the valve body as well as those of the leaflet occluders. Due to concerns with respect to manufacturing costs, which are directly related to manufacturing tolerances, alternative arrangements for providing a purging flow around the leaflet occluders, particularly at their hinged connections to the valve body, in a manner which conserves hemodynamic energy, is still being sought after.

SUMMARY OF THE INVENTION

It is an object of the present invention to provide a bi-leaflet heart valve prosthesis with reduced closing time.

Another object according to the present invention is to provide a heart valve prosthesis having an improved purging flow around the leaflet occluders and their mounting parts in a cost effective manner.

Another object of the present invention is to provide a heart valve prosthesis attaining objectives of the types cited above, while being quiet in operation and having an improved low friction movement of the leaflet occluders between their open and closed positions.

These and other objects will become apparent from studying the appended description and drawings which relate to a heart valve prosthesis comprising:

a generally annular valve body having an interior surface defining a central passageway through which blood flows;

a pair of leaflet occluders proportioned to be pivotally received within said valve body and to move between an open position permitting blood flow in a downstream direction and a closed position blocking the reverse flow of blood in an upstream direction, said leaflet occluders each having a generally flat upstream surface, an opposed generally concave downstream surface, a diametral edge between the upstream and downstream surfaces for mating with the other occluder and an arcuate edge also between the upstream and downstream surfaces opposite the diametral edge and said occluders further comprising a pair of opposed outwardly protruding mounting ears adjacent the diametral edge for pivotal mounting to said valve body, said mounting ears having a generally part-spherical upstream surface, and an opposed downstream surface; and said valve body defining for each leaflet occluder, a pair of recesses each having a varying depth extending into the valve body, and each recess forming a generally crescent-shaped opening in the valve body inner surface, each said recess further including first and second opposed arcuate end portions with a sidewall extending between said end portions for engaging an upstream surface of a leaflet mounting ear at least during valve closing and a generally opposed rounded convex surface adjacent a downstream end of the recess for guiding the downstream surface of said leaflet mounting ear at least during valve opening.

Other aspects of the present invention are provided in a heart valve prosthesis of the above type, but having a valve body which defines for each leaflet occluder, a pair of recesses each having a varying depth extending into the valve body, and each recess forming a generally crescent shaped opening in the valve body inner surface, each said recess further including first and second opposed arcuate end portions on either side of a relatively deeper central depression dimensioned to receive a leaflet ear therein for pivotal mounting thereof, the first and second end portions sloping from the valve body inner surface in the direction of depth of the recess toward the central depression, said recess end portions defining passageways spaced from an edge portion of a leaflet mounted in the intermediate depression of the recess, so as to form a path for a flow of blood around the leaflet edge portion.

BRIEF DESCRIPTION OF THE DRAWINGS

Referring now to the drawings, wherein like elements are referenced alike,

FIG. 1 is a perspective view of a heart valve prosthesis illustrating certain aspects of the present invention;

FIG. 2 is a cross-sectional view taken along the line 2—2 of FIG. 1, showing the valve in an open position;

FIG. 3 is a cross-sectional view similar to that of FIG. 2 but showing the valve in closed position;

FIG. 4 is a fragmentary view taken partly in cross-section along the line 4—4 of FIG. 2;

FIG. 5 is a fragmentary cross-sectional view taken along the line 5—5 of FIG. 2;

FIG. 6 is a fragmentary side elevational view showing the central portion of the valve body of FIGS. 2 and 3 on an enlarged scale;

FIG. 7 is an exploded fragmentary perspective view illustrating an alternative embodiment of a leaflet occluder-mounting recess, and a leaflet occluder mounted therein;

FIG. 8 is a fragmentary plan view of one corner of the leaflet of the preceding Figures showing the mounting ear thereof in greater detail;

FIG. 9 is a fragmentary elevational view of the leaflet of the preceding Figures showing the mounting ear thereof in greater detail; and FIG. 10 is an end elevational view of the leaflet of the preceding Figures.

DETAILED DESCRIPTION OF THE PREFERRED EMBODIMENT

Referring now to the drawings, a heart valve prosthesis is generally indicated at 10. The prosthesis 10 includes a generally annular valve body 12, having an upper surface 13 and an inner cylindrical surface 14. Disposed within the valve body are a pair of leaflet occluders, or leaflets, generally indicated at 16. The leaflets 16, as will be seen, are mounted for both pivoting and transitional movement between opened and closed positions.

The outside surface of valve body 12 includes an annular recess or depression 20 for accommodating a suturing ring (not shown) of a conventional type for suturing the heart valve 10 to the heart tissue. As will be seen, the hinge mechanism supporting the leaflet 16 is protected by the valve body against contact with heart tissue or any unraveled sutures which might be present in the immediate area.

The leaflets 16 have an outer edge which extends between upstream and downstream surfaces. The outer edge includes an inner diametrical edge portion 24 which is opposed by an arcuate, and more particularly a semicircular edge portion 26. According to one aspect of the present invention, the upstream major surfaces 30 of leaflets 16 are generally flat and semicircular in shape. The opposed downstream surface 32 is generally concave in shape, and is preferably part cylindrical in configuration, with the axis of the cylinder lying below the leaflet in a mid plane of the leaflet which extends normal to both the leaflet upper surface and the leaflet diametrical edge portion 24. The leaflets 16 are preferably symmetrical about the mid plane thereof. The concave downstream surface 32 is shown in the perspective view of FIG. 1, and is best seen in FIG. 10, which also shows the leaflet symmetry.

When in the fully open position of FIG. 2, the leaflets 16 present a minimal impedance to blood flowing in the downstream direction of arrow 120. The concave configuration of downstream leaflet surfaces 32 provides increased clearance for blood flow in a downstream direction, as compared to relatively flat leaflets of comparable thickness adjacent their diametrical or mating ends.

As mentioned, the leaflets 16 preferably each have a relatively flat upstream surface 30. This enhances the stiffness of the leaflet to withstand bending deflections which could "cup" the leaflet, effectively shortening the distance between its opposed mounting ears 54 and thus increasing the possibility that the ears might become disengaged from the recesses 48. Such cupping, if allowed to occur, would likely be in a direction tending to exaggerate the concavity of the downstream surface. The increased stiffness provided by the relatively flat upstream surface effectively precludes such bending and any attendant dislodgement of the leaflet from the valve body.

As mentioned above, the valve body 12 has a generally annular configuration with an inner cylindrical surface 14. The cylindrical surface 14 extends throughout most of the valve body interior, except for raised flat surfaces 44 which are generally parallel to one another, extending across chords of the inner cylindrical surfaces 14, and having a valve body mid plane extending along the diametrical plane of body 12 at which edge portions 24 are mated upon valve closing. As will be seen, the heart valve prosthesis of the preferred embodiment is symmetrical about the valve body mid plane, with the recesses and leaflets being mirror images of one another. Recesses 48 are formed in flat surfaces 44 to provide a hinge mounting for the leaflets 16. Two recesses are required for the mounting of each leaflet, and are located adjacent the diametrical edge of that leaflet.

Recesses 48 formed in the annular valve body have a generally crescent shaped opening in flat surface 44 and a generally part spherical interior, or end wall shape complementing that of the part spherical leaflet ears. The recesses are enlarged with respect to the mounting ears to provide smooth, low friction operation of the leaflet during opening and closing with a considerable portion of the leaflet travel comprising a transitional "floating" which is substantially free of frictional engagement with the recess mating edges. FIG. 2 illustrates the preferred location of recesses 48 which maintain the diametral edges 24 of the leaflet below the upper surface 13 of valve body 12 so as to avoid any contact with heart tissue.

As will be seen herein, the recesses 48 provide an improved wash flow over the leaflet mounting parts. The wash flow originates in high pressure regions, along tipped or pointed recess end portions. Wash flow is thereafter developed along particularly contoured recess sidewall and endwall surfaces, exiting at a central, upstream portion of the recess which is broadened to provide the aforementioned translational shifting of the leaflets in addition to a low pressure outlet for the wash flow.

Referring briefly to FIG. 4, the arcuate edge portion 26 of a leaflet is blended into a relatively flat, lateral edge portion 50 adjacent the diametrical edge portion 24. The lateral edge portion 50 provides a relatively close fit with respect to the flat surface 44. According to one aspect of the present invention, the relative size of flat surface 44 as compared to the inner cylindrical surface 14, is made as small as possible to minimize impeding blood flow through the heart valve prosthesis and to also minimize turbulence in the flow. Generally part spherical outward projections or mounting ears 54 extend from the flat edge portions 50 of a leaflet. The ears 54 have downstream and upstream surfaces 53,55 and an outer, generally circular free edge 56 which extends toward the interior of recess 48. As can be seen with further reference to FIGS. 8 and 9, the upper surfaces 55 of the mounting ears 54 are part spherical and in the preferred embodiment are quarter-spherical in configuration. The mounting ear upstream surface 55 is spherical while the lower surface 53 has a relatively flat, generally planar surface configuration.

Referring now to FIGS. 2 and 3, the leaflets 16 are moved between open and closed positions in response to blood flow through valve 10. In the open position of FIG. 2, the mounting ears 54 are seated in a first end portion 70 of recesses 48. As the cardiac cycle continues, the leaflets 16 move to the closed position illustrated in FIG. 3. In the closed position, the ears 54 are positioned adjacent a second end portion 72 of recesses 48. Referring to FIG. 2, the centerline plane CL of the heart valve divides or separates the recesses associated with two different leaflets. Thus, the two recesses illustrated in FIG. 2 each support only first edges of respective leaflets.

As will become apparent herein, the upstream and downstream surface configurations of leaflets 16 offer a number of advantages. For example, the relatively flat upstream surface 30 imparts a stiffness to the leaflets, preventing their unintentional disengagement from a pivotal mounting connection with the valve body. Referring to FIG. 2, the prosthesis 10 is shown in a generally open configuration with the axes of the generally cylindrical downstream surfaces extending generally in the direction of blood flow, indicated by arrow 120. The generally concave cylindrical downstream surfaces 32 provide, in addition to a streamlining effect, a leaflet of reduced cross sectional thickness, thereby aiding in eliminating a drag of the blood flow on the leaflet surfaces.

Referring to FIG. 10, leaflet 16 is shown in an end elevational view, facing the diametrical edge 24 of the leaflet. The upper, generally flat surface 30 extends between the lateral edges 50 of the leaflet. In the preferred embodiment, the generally part cylindrical downstream surface 32 extends nearly the same distance, that is, immediately adjacent the lateral edges 50 of the leaflet, but preferably is extended by relatively flat portions 53. The flat extensions 53 can be eliminated, if desired. As can be seen in FIG. 10, the leaflet midplane thickness $t_1$, taken along a central plane of the leaflet, is substantially smaller than the thickness $t_2$ taken at the leaflet lateral edge. The generally part spherical mounting ears 54 have a base at their point of mounting to the leaflet body no larger than the thickness $t_2$ at the lateral edge of the leaflet body so as to avoid any protrusion beyond the upstream or downstream surfaces 30, 32 of the leaflet. The mounting ears 54 are located adjacent the diametrical edge 24 and extend outwardly from the lateral edges 50 in generally opposite directions.

The different curvatures of the upper and lower surfaces of the leaflet conveniently provide regions of increased strength immediately adjacent the mounting ears 54 where the stresses are high while significantly reducing the mass of the leaflet at the central portion thereof. As will be seen, leaflet cross-sectional configurations corresponding generally to the shape illustrated in FIG. 10, provide other advantages which improve valve operation. For example, the configuration of the leaflet cross section provides a leaflet of reduced, minimal mass whose upper surface increases stiffness and prevents disengagement of the leaflet mounting with the valve body. The downstream surface configuration reduces leaflet mass and improves the capture of blood flow with an attendant application of force to the downstream surface of the leaflet, thereby accelerating valve closing and lessening regurgitation. Further, the leaflet cross-sectional configuration conveniently provides lateral edges of localized increased mass immediately adjacent the leaflet mounting ears where stress on the leaflet is high.

Referring now to FIG. 6, recesses 48 include first and second opposed, generally arcuate end portions 70, 72 respectively. The first end portion 70 is located remote from the centerline CL of the prosthesis, and the second end portion 72 is located proximate that centerline. Disposed between the end portions is a central depression 76 terminating in a generally ovoid end wall 78. A sloping or bevelled, generally arcuate side wall 80 extends between the end portions 70, 72. Side wall 80 includes a first, relatively deeper arcuate edge 84 interior to the recess and a second arcuate perimetrical edge 86. Side wall 80 forms a recess spaced from the adjoining leaflet lateral edge portion 50 so as to provide a pathway for a wash flow across the leaflet edge, when the leaflets are in a closed position.

A generally hook shaped perimetrical edge 88, located at the downstream end of the recess, also extends between the first and second end portions 70, 72 and cooperates with edge 86 to form the outer periphery of recess 48 at a point where the recess opening is blended with the raised side portion 44. The edge 88 includes a first curved portion 89 located at an end of a rounded convex guide surface 95 of the recess and a generally straight line portion 91 located at one end of a generally flat stop surface 97 of the recess.

The first end portion 70 also includes a bump or projection 92 which protrudes above the surface of sidewall 80. Projection 92 extends throughout the entire width of side wall 80, between edges 84, 86 of the side wall. The configuration of side wall 80, with the exception of the projection 92, is generally part spherical in cross section so as to form an intimate engagement with the upper surface of mounting ears 54. With reference to the surface of sidewall 80, projection 92 forms a reentrant bend which extends toward the central depression 76.

The first end portion 70 of the recess includes a tip 100 which is generally bulbous at its outer periphery, partly due to the rounding effect of the reentrant bend of projection 92. An outward excursion 102 in the first, deeper recess edge 84 provides a channel for wash flow circulating in a generally upstream direction originating at tip 100 and extending inwardly to the central depression 76 and upwardly across the face of side wall 80. As mentioned, a wash flow is present even when the leaflets are in the closed position illustrated in FIG. 3.

The second end portion 72 has a more sharply pointed tip 106 at which the generally arcuate recess edges 86,88 are terminated. Tip 106 of recess portion 72 channels a wash flow across the recess end portion, toward the upper portion of recess 48.

When the leaflets are in the open position of FIG. 2, a small part of the relatively large downstream flow is directed across the leaflet edges and the leaflet mounting recesses 48. With the leaflets in the closed position of FIG. 3 blood flow in an upstream direction is blocked, except for a wash flow entering at the tips 100,106 of the recess end portions 70,72, respectively, as indicated arrows 112 of FIG. 3. Wash flows entering the tips 100,106 are collected at the upper portion of the leaflet recess where the wash flow exits, as indicated by arrows 114.

As can now be seen, the outer, perimetrical edges 86,88 of recess 48 form a generally C-shaped or crescent-shaped opening in the raised portion 44 of valve body 12. The generally C-shaped opening of recess 48 results from the aforementioned generally arcuate end portions 70, 72 and the intermediate or central depression 76 which forms a portion of the edge 88 of the recess. The outer perimetrical edges 86, 88 of the recess are blended with the flat surface 44 of the valve body, with the recess extending varying amounts in the direction of its depth, generally normal to the flat surface 44. End portions 70, 72 and tips 100, 106 are blended at one end with the raised surface 44 and extend at their other ends with a generally increasing depth toward the central depression 76.

The deepest portion of recess 48 is located at the central depression 76. The central depression 76 is bounded by interior edge 84 located in interior portions of the recess, and is also bounded by a portion of the outer perimetrical edge 88 of the recess. The end wall 78 at the deepest part of the recess 76 lies immediately adjacent the free edge 56 of the leaflet mounting ear, but is preferably spaced apart therefrom, as illustrated in FIG. 4, for example. The side wall 80 extends throughout the first and second end portions 70, 72 and is bounded at its outside by perimetrical edge 86 and is bounded at its inside by interior edge 84. The side wall 80 accordingly has an outer edge at the surface 44 of the valve body and a second, deeper edge 84 recessed below flat surface 44.

As mentioned above, the cross-sectional profile of side wall 80 is generally part circular (see FIGS. 4 and 5) so as to mate with the part spherical profile of the upper surface of mounting ears 54, as illustrated in FIG. 10. As can be seen in FIGS. 2 and 3, the recess 48 has an opening of lateral width greater than the size of the ears 54 so as to allow the ears to travel back and forth, toward and away from centerline plane CL as well as upstream and downstream, during leaflet opening and closing. The increased width of the recess provides a clearance which helps to eliminate binding of the ears in their extreme closed and open positions (see FIGS. 2 and 3, respectively). The projections 92 also help to prevent binding of the leaflets as the leaflets are moved to a fully open position.

If desired, the interior edge 84 and the wall 78 surrounded by that edge can be eliminated, with the sidewall 80 being blended with guide surface 95 and the stop surface 97. An example of a recess 49 having this arrangement is shown in FIG. 7, and is particularly suitable for leaflets having a spherical configuration. As before, it is preferred that the edge of the leaflet mounting ear be spaced from the recess wall surfaces. Except for the absence of interior edge 84 and the endwall 78, recess 49 is similar to recess 48.

With reference to FIGS. 2 and 3, operation of the valve will now be described. As will be seen, the leaflet mounting ears 54 undergo both a pivoting and a translation displacement as they are moved between their closed and open positions.

In FIG. 2 the valve is illustrated in an open configuration, with blood flowing in a downstream direction indicated by arrow 120. The leaflet ears 54 are nested in the first end portion 70 of recess 48 with the lower surface 53 of the leaflet contacting the stop surface 97, which, in end view, is visible as the straight edge portion 91 of perimetrical edge 88. In the fully opened position, the upper surface 55 of the leaflet mounting ear contacts the projection 92 so as to prevent wedging of the upper surface of the mounting ear and the end portion 70 as the ear is seated in its open position. As shown in FIG. 4, the outer edge 56 of the leaflet mounting ear is spaced from the inner end of side wall 80. As back pressure is exerted on the downstream surface 32 of the leaflets, the leaflets are pivoted such that their lower free ends 26 are swung in outward directions corresponding to a pivoting of ears 54 within the recesses.

When the direction of blood flow reverses, toward an upstream direction (opposite to that of arrow 120), blood flow is captured by the generally cylindrical lower surface 32 of the leaflet, creating a closing force for the leaflets. The concave downstream surfaces of the leaflets enhance the capture of blood flow under the leaflet and discourage bypass of the back flow around the lower ends of the leaflets, as is more likely to occur with leaflets having generally flat downstream surfaces. Due to the increased capture of blood flow, the force applied to the leaflet downstream surfaces is increased and the leaflets are closed more quickly, thus decreasing the amount of regurgitation in each cardiac cycle.

As the leaflets are moved toward the position of FIG. 3, the configuration of recesses 48 allows the leaflets to undergo translational movement in upward and inward directions. While the leaflets are lifted in an upstream direction, contact is established between the upper surface 55 of the mounting ear and side wall 80 of recess 48, with the bottom surface 53 of the leaflet being raised out of contact with perimetrical edge 88. The leaflet's mounting ears continue to follow side wall 80 as they close, and the leaflet closing motion is stopped as the diametral edges 24 of the leaflets engage one another. The bottom, arcuate edges of the leaflets are bevelled and, in the final portion of their upstream travel, the arcuate leaflet edges seat against the lower portion of the valve body inside surface 14. Upon a reversal of blood flow direction as the cardiac cycle continues, the closed leaflets have a downstream pressure applied thereto at the start of an opening operation. During opening, downstream directed blood flow applies force against the upstream surfaces 30 of the leaflets. Due to the positioning of their pivot mounting, leaflets 16 are subjected to a relatively large torque, as a result of forces applied across the upstream surfaces of the leaflets. This results in a relatively rapid initial opening of the leaflets which easily overcomes any resistance thereto. The opening force also breaks the seal between the diametrical edge portions 24 of the leaflets, and between their lower bevelled edges 26 and the inside valve surface 14.

Due to the afore-described configuration of the recesses 48, the leaflets initially undergo a downstream translational and pivoting displacement. The downstream translation continues for a brief portion of time until the ears 54 engage the lower end of recess side wall 80, as illustrated in FIGS. 2 and 4, and in particular, they engage the convex guide surface 95. Inward swinging of the leaflets is initiated, and continues until the downstream edges of the leaflets contact the recess stop surface 97.

On opening of the leaflets, contact is broken between the upper surface 55 of the mounting ears and side wall 80, it being appreciated that the recess is dimensioned larger than the mounting ear received therein to allow for such translation. Leaflet displacement, including continued rotational and translational displacement continues until the leaflet lower surface 53 contacts stop surface 97 and the upper surface 55 of mounting ear 54 comes into contact with projection 92. The fully open leaflet configuration of FIG. 2 is then achieved.

When the downstream surface 53 of the leaflet mounting ears contacts the rounded portion of convex surface 95, the leaflet mounting ears begin a rolling motion. This rolling contact is established between the bottom surface of the leaflet mounting ear and convex surface 95, it being emphasized that contact between the leaflet mounting ear and the valve recess is not limited to a point at the perimetrical edge of the recess but rather comprises a line contact extending substantially the full depth of that recess.

The projection 92 also acts with a moderate braking force on the leaflets prior to contact of the underneath surface 53 with the straight edge portion 91 of the recess, thus significantly reducing the noise of the leaflets when seated in their fully open position. The configuration of the mounting ears and of the recess 48 has also been found to provide a relatively quiet closing of the leaflets. It is important that the heart valve prosthesis provides a quiet operation considering the improved response times provided by the leaflet and recess configurations.

As was pointed above, recess 48 provides a channel for wash flow around the leaflets 54, adjacent the central depression of the recess. It has been found that the wash flow pattern created by the end portions 70,72, especially the tips 100,106 thereof has been very effective in purging the moving components of the heart valve prosthesis. It has been found that the wash flow has a relatively high pressure at the entrances to recess 48, namely, the end portions 70,72 thereof. The pressure of the exiting flow indicated by arrows 114 is substantially lower. This arrangement has been found to provide a very effective and efficient washing or purging of the valve body recess and mounting ear portions of the leaflets.

As will now be seen, the preferred configuration of leaflets 16 provide several advantages in a leaflet design of relatively minimal mass. First, the concave downstream surface configuration of the leaflets captures blood flow and increases force applied to the leaflets accelerating their closing and thereby lessening regurgitation through the valve. The relatively flat upstream surface of the leaflets increases their stiffness, and greatly improves resistance to bending thus ensuring the captivity of the leaflet mounting ears within the recesses of the valve body. This is an important advantage particularly for relatively thin leaflets which can be constructed from material sufficiently flexible to permit their snap-in installation. This of course cooperates with the capture of upstream blood flow effectively allowing the leaflets to close promptly.

The preferred leaflet configuration, where leaflet thickness is increased at the lateral edges, also provides a mounting surface for the mounting ears of increased size, thus ensuring that the mounting ears do not protrude beyond the upstream and downstream major leaflet surfaces. This latter feature is particularly important for the preferred part spherical mounting configuration which has an enlarged base portion at its point of joinder with the leaflet edge. The part spherical mounting ears reduce lateral play of the leaflet despite inevitable wear experienced throughout the patient's life. Reduced wear, especially compared to that of spherical mounting ears, maintains control over leaflet movement and prevents erratic leaflet operation such as asynchronous closing.

Several variations in the above-described embodiment are possible. For example, the leaflet mounting ears and the recesses within which they are mounted can be angularly offset corresponding amounts with respect to the leaflet body and valve body, respectively, while preserving the various angular orientations that exist throughout the range of motion of the leaflets within the valve body. More specifically, the spherical ears 54 can have their bottom surfaces 53 inclined at an angle to the upper leaflet surface 30 and the recesses 48 can be repositioned so as to rotatively displace their openings in the raised flat surface 44 of the leaflet body. This variation will maintain a given angle between the leaflets, when in their closed position. In addition, the leaflets 16 can be disposed at any angle to the valve body that may be desired. However, the angular displacement illustrated in FIG. 3 is generally preferred to provide a desired rapid response time in leaflet movement, an efficient utilization of hemodynamic energy to move the leaflets between their opened and closed positions, and to help prevent wedging of the leaflets within the valve body when brought to their closed position.

A description of the present forms of the invention having been described by way of example, it is anticipated that further variations of the described forms of the apparatus may be made without departing from the invention and the scope of the appended claims.

What is claimed is:

1. A heart valve prosthesis comprising:
   a generally annular valve body having an interior surface defining a central passageway through which blood flows;
   a pair of leaflet occluders proportioned to be pivotally received within said valve body and to move between an open position permitting blood flow in a downstream direction and a closed position blocking the reverse flow of blood in an upstream direction, said leaflet occluders each having a generally flat upstream surface, an opposed generally concave downstream surface, a diametral edge between the upstream and downstream surfaces for mating with the other occluder and an arcuate edge also between the upstream and downstream surfaces opposite the diametral edge and said occluders further comprising a pair of opposed outwardly protruding mounting ears adjacent the diametral edge for pivotal mounting to said valve body, said mounting ears having a generally part-spherical upstream surface, and an opposed downstream surface about which the leaflet is rolled; and said valve body defining for each leaflet occluder, a pair of recesses each having a varying depth extending into the valve body, and each recess forming a generally crescent-shaped opening in the valve body inner surface, each said recess further including first and second opposed arcuate end portions with a sidewall extending between said end portions for engaging an upstream surface of a leaflet mounting ear at least during valve closing and a generally opposed rounded convex surface adjacent a downstream end of the recess for guiding the downstream surface of said leaflet mounting ear at least during valve opening.

2. The heart valve prosthesis of claim 1 wherein each said recess further includes a central depression intermediate the recess end portions, said central depression forming a bottom wall of said recess, spaced from and immediately adjacent to a free end of a leaflet ear received in said recess, the first and second end portions sloping from the valve body inner surface in the direction of depth of the recess toward the central depression, said recess end portions defining passageways spaced from an edge portion of a leaflet mounted in the intermediate depression of the recess, so as to form a path for a flow of blood around the leaflet edge portion.

3. The heart valve prosthesis of claim 1 wherein said mounting ears are generally part spherical in configuration with a generally upwardly facing part spherical surface.

4. The heart valve prosthesis of claim 1 wherein said recesses further comprise a sloping arcuate sidewall, extending between said first and second ends, said sidewall having a first, deeper arcuate edge located remote from said valve body inner surface and surrounding said central depression and a second, relatively larger arcuate edge blended with said valve body inner surface and disposed about said deeper arcuate edge.

5. The heart valve prosthesis of claim 1 further comprising an elongated ear-engaging member protruding from said sidewall toward said leaflet, adjacent one end portion of said recess.

6. The heart valve prosthesis of claim 1 wherein said first recess end is terminated with a generally V-shaped opening in said valve body inner surface and said lobe is located adjacent said second recess end.

7. The heart valve prosthesis of claim 1 wherein said downstream surface is generally part cylindrical.

8. The heart valve prosthesis of claim 1 wherein said arcuate edge is generally semicircular.

9. The heart valve prosthesis of claim 1 wherein the leaflet occluders further comprise relatively flat lateral edge portions between the arcuate and the diametral edge portions thereof, said mounting ears outwardly protruding from said flat lateral edge portions.

10. The heart valve prosthesis of claim 1 wherein the central depression has a generally ovoid end wall.

* * * * *